United States Patent [19]
Talpade

[11] Patent Number: 6,110,100
[45] Date of Patent: *Aug. 29, 2000

[54] SYSTEM FOR STRESS RELIEVING THE HEART MUSCLE AND FOR CONTROLLING HEART FUNCTION

[75] Inventor: Dnyanesh Talpade, Plymouth, Minn.

[73] Assignee: Scimed Life Systems, Inc., Maple Grove, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/064,370

[22] Filed: Apr. 22, 1998

[51] Int. Cl.$^7$ ............................... A61F 2/00; A61N 1/05
[52] U.S. Cl. ........................... 600/37; 600/373; 600/374; 600/375; 600/393; 607/119; 128/897; 606/151

[58] Field of Search ................................ 600/16, 37, 373, 600/374, 375, 381, 393, 534, 595; 607/119, 129, 130; 128/897; 606/151, 228

[56] References Cited

U.S. PATENT DOCUMENTS

| | | |
|---|---|---|
| 3,455,298 | 7/1969 | Anstadt . |
| 4,030,509 | 6/1977 | Heilman et al. ........................... 607/17 |
| 4,144,889 | 3/1979 | Tyers et al. .............................. 607/130 |
| 4,536,893 | 8/1985 | Parravicini . |
| 4,685,446 | 8/1987 | Choy . |
| 4,781,716 | 11/1988 | Richelsoph . |
| 4,817,586 | 4/1989 | Wampler . |
| 4,846,831 | 7/1989 | Skillin . |
| 4,861,330 | 8/1989 | Voss . |
| 4,863,461 | 9/1989 | Jarvik . |
| 4,888,011 | 12/1989 | Kung et al. . |
| 4,902,291 | 2/1990 | Kolff . |
| 4,906,229 | 3/1990 | Wampler . |
| 4,919,647 | 4/1990 | Nash . |
| 4,925,377 | 5/1990 | Inacio et al. . |
| 4,925,443 | 5/1990 | Heilman et al. . |
| 4,936,857 | 6/1990 | Kulik . |

(List continued on next page.)

FOREIGN PATENT DOCUMENTS

| | | |
|---|---|---|
| 10094557 | 7/1983 | U.S.S.R. . |
| WO 98/17347 | 4/1998 | WIPO . |
| WO 99/44534 | 10/1999 | WIPO . |

OTHER PUBLICATIONS

"Mechanisms of Contraction", *Human Physiology*, Fourth Edition, by Stuart Ira Fox, pp. 300–323.

"The Management of Chronic Heart Failure", by Jay N. Cohn, M.D., *The New England Jouranl of Medicine*, pp. 490–498, Aug. 15, 1996.

"Reversal of Chronic Ventricular Dilation in Patients With End–Stage Cardiomyopathy by Prolonged Mechanical Unloading", by Howard R. Levin, M.D. et al., pp. 2717–2718, vol. 91, No. 11, Jun. 1, 1995.

"The Nature of the Atrial Receptors Responsible for a Reflex Decrease in Activity in Renal Nerves in the Dog", by R.J. Linden, D.A.S.G. Mary and D. Weatherill, *The Physiological Society*, 1980, pp. 31–40.

"Control of Sympathetic Nerve Activity by Vagal Mechanoreflexes is Blunted in Heart Failure", by Mark E. Dibner–Dunlap, M.D. and Marc D. Thames, MD, vol. 86, No. 6, Dec. 1992, pp. 1929–1934.

"Baroreflex Regulation of Regional Blood Flow in Congestive Heart Failure", by Mark A. Creager et al., *The American Physiological Society*, 1990, pp. H1409–H1414.

*Primary Examiner*—Linda C. M. Dvorak
*Assistant Examiner*—Brad C. Blaise
*Attorney, Agent, or Firm*—Joseph R. Kelly; Westman, Champlin & Kelly, P.A.

[57] ABSTRACT

An apparatus and method for relieving stress on a heart muscle tissue in a wall of a heart having a chamber. A plurality of biocompatible and implantable elongate strips are configured to be connected to the heart wall and disposed about the chamber such that the elongate strips are arranged in spaced relation to one another. The elongate strips are bendable and are sufficiently resistant to elongation such that natural stretching of the heart wall does not cause elongation of the plurality of strips.

36 Claims, 5 Drawing Sheets

U.S. PATENT DOCUMENTS

| | | |
|---|---|---|
| 4,938,766 | 7/1990 | Jarvik . |
| 4,957,477 | 9/1990 | Lundback . |
| 5,067,960 | 11/1991 | Grandjean . |
| 5,069,680 | 12/1991 | Grandjean . |
| 5,089,019 | 2/1992 | Grandjean . |
| 5,098,442 | 3/1992 | Grandjean . |
| 5,119,804 | 6/1992 | Anstadt . |
| 5,131,905 | 7/1992 | Grooters ................................ 600/16 |
| 5,167,628 | 12/1992 | Boyles . |
| 5,205,810 | 4/1993 | Guiraudon et al. . |
| 5,290,227 | 3/1994 | Pasque . |
| 5,326,374 | 7/1994 | Ilbawi et al. . |
| 5,332,403 | 7/1994 | Kolff . |
| 5,358,519 | 10/1994 | Grandjean . |
| 5,364,337 | 11/1994 | Guiraudon et al. . |
| 5,383,840 | 1/1995 | Heilman et al. . |
| 5,406,946 | 4/1995 | Imran ..................................... 600/374 |
| 5,411,025 | 5/1995 | Webster, Jr. ........................... 600/374 |
| 5,425,364 | 6/1995 | Imran ..................................... 600/374 |
| 5,429,584 | 7/1995 | Chiu . |
| 5,447,533 | 9/1995 | Vachon et al. ......................... 607/120 |
| 5,484,385 | 1/1996 | Rishton . |
| 5,505,701 | 4/1996 | Anaya Fernandez de Lomana . |
| 5,558,617 | 9/1996 | Heilman et al. . |
| 5,598,848 | 2/1997 | Swanson et al. ...................... 600/508 |
| 5,702,343 | 12/1997 | Alferness . |
| 5,961,440 | 10/1999 | Schweich et al. . |

SYSTEM FOR STRESS RELIEVING THE HEART MUSCLE AND FOR CONTROLLING HEART FUNCTION

BACKGROUND OF THE INVENTION

The present invention deals with treatment of heart disease. More particularly, the present invention deals with a system and method for treating heart disease by regulating blood flow in the vasculature.

Congestive heart failure is a common heart disease. The prevalence of incidents of congestive heart failure has recently increased, and there is considerable morbidity and mortality associated with its diagnosis. In fact, congestive heart failure is an extremely lethal disease with an estimated five year mortality for a vast majority of both men and women who encounter the disease.

Congestive heart failure results from loss of, or impairment of, normal heart function. This loss or impairment reduces cardiac output. This, in turn, results in a reduction in both blood flow and blood pressure in the kidneys. This reduction in flow and pressure causes a renin-angiotensin response that exacerbates congestive heart failure.

Briefly, as blood flow and pressure is reduced in the kidneys, cells in the kidneys referred to as juxtaglomerular apparatus secret an enzyme referred to as renin into the blood. The enzyme renin cleaves a ten-amino acid polypeptide called angiotensin I from a plasma protein in the blood called angiotensinogen. A converting enzyme in the blood removes two amino acids from the angiotensin I polypeptide leaving an eight amino acid polypeptide called angiotensin II. Angiotensin II has numerous effects on the smooth muscle layers of arterioles, including causing vasoconstriction. Further, an indirect effect of an increase in angiotensin II increases blood volume. Blood volume is increased because angiotensin II stimulates secretion of aldosterone from the adrenal cortex which, in turn, causes an increase in salt and water retention in the kidneys. Angiotensin II also stimulates thirst centers in the hypothalamus causing more water to be ingested. The increase in blood volume and the corresponding vasoconstriction cause an increase in blood pressure and hence a volume overload on the heart which causes further deterioration of the heart condition.

Another response is also related to congestive heart failure. Baroreceptors, referred to as stretch receptors, reside in the aortic arch and carotid sinuses. The baroreceptors are essentially pressure sensors sensing blood pressure in that area. The baroreceptors provide physiological feedback in two ways. First, in response to a reduction in blood pressure, the baroreceptors provide a neurohormonal feedback response which acts to increase the heart rate in an attempt to increase cardiac output. The increased heart rate causes the heart to work harder which, in turn, causes the heart muscle to stretch further. Also, a reduction in pressure caused by a reduction in cardiac output causes the baroreceptors to provide a feedback response which acts to constrict the distal vasculature thus increasing pressure in that area.

It can thus be seen that impairment of heart function can lead to a cyclical feedback response which increases, rather than reduces, the impairment. Such a cyclical feedback response is sometimes referred to as a cascade.

For instance, if the heart muscle is stressed, the heart works harder and begins to stretch. This reduces the efficiency of the heart in the following way. Muscles are thought of as being composed of many fibers which contract and lengthen to accomplish muscular action. Each fiber includes many densely packed subunits referred to as myofibrils which are on the order of 1 μm in diameter and extend in parallel from one end of the muscle fiber to the other. Each myofibril has spaced regions of thick filaments (about 110 Å thick) and thin filaments (about 50–60 Å thick). The thick filaments are formed of a protein, myosin, and the thin filaments are formed of a protein, actin. The actin and myosin filaments overlap in regions periodically spaced along the myofibrils. The units in the repeated overlapping pattern are referred to as sarcomeres.

Contraction of a muscle fiber results from shortening of the myofibrils which form the muscle fiber. The myofibrils are shortened, but the individual filaments in the myofibrils do not decrease in length. Instead, the actin and myosin filaments slide longitudinally relative to one another to shorten the overall length of the myofibrils. Sliding occurs as a result of cross-bridges extending from the myosin toward the actin attaching to the actin at bonding sites. The cross bridges are oriented to draw overlapping actin filaments on either longitudinal side of the myosin filament toward the longitudinal center of the myosin filament. When the muscle fiber is stretched such that the actin and myosin only overlap a short distance, only a small number of cross-bridges are available for bonding to the adjacent actin, and contraction is highly inefficient. When the muscle is stretched to a point where the actin and myosin filaments no longer overlap, contraction is rendered impossible.

This inefficient or impaired heart function causes blood pressure in the areas of both the kidneys and the baroreceptors to decrease. The feedback response generated by the kidneys causes further overload and stress on the heart. The feedback response generated by the baroreceptors causes increased heart rate. Both of these feedback responses cause the heart to work harder, causing further stretching of the heart muscle and thus leading to greater inefficiencies. In response, the feedback responses become even more acute—and the cascade continues.

This cascade effect, which is a natural progression of congestive heart failure, leads to increased muscle mass and stretching of the heart muscle fibers which, in turn, leads to muscular hypertrophy of the left ventricle. The hypertrophy is a compensatory mechanism which, if maintained at a given level such that muscle fibers maintain inherent contractile properties (i.e., actin-myosin overlap), can be beneficial for maintaining proper heart function. However, prolonged and continuous stretching causes muscular fatigue and reduced muscle performance as explained by the known Frank-Starling mechanism.

SUMMARY OF THE INVENTION

An apparatus and method restrict elongation of heart muscle tissue in a wall of a heart having a chamber. A plurality of biocompatible and implantable elongate strips are configured to be connected to the heart wall and disposed about the chamber such that the elongate strips are arranged in spaced relation to one another. The elongate strips are bendable and are sufficiently resistant to elongation such that natural stretching of the heart wall does not cause elongation of the plurality of strips.

DETAILED DESCRIPTION OF THE PREFERRED EMBODIMENTS

Figure 1A:
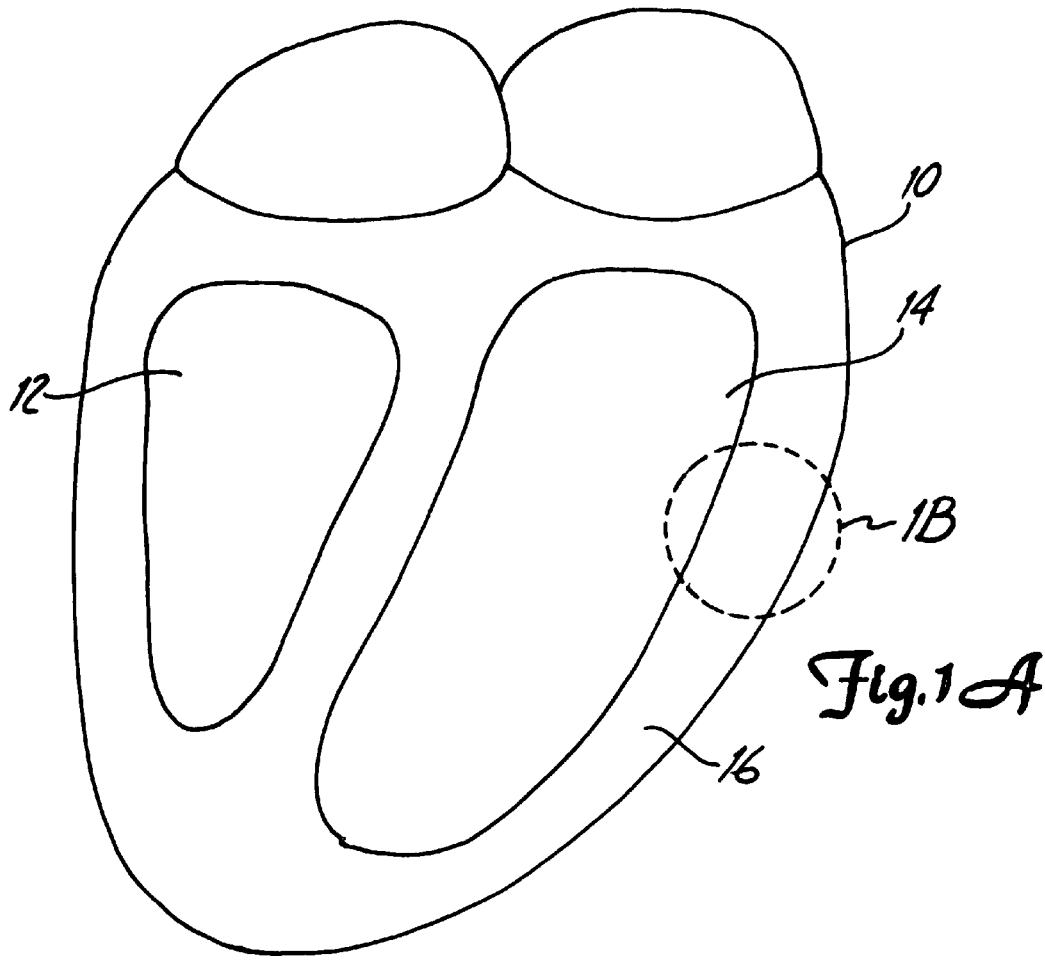
FIG. 1A is a side sectional view of a heart.

FIG. 1A illustrates a portion of a heart 10. FIG. 1A illustrates a plurality of chambers in heart 10 including right ventricle 12 and left ventricle 14. FIG. 1A also illustrates heart wall 16 which extends around chambers 12 and 14, and separates chambers 12 and 14. As discussed in the background portion above, congestive heart failure can lead to hypertrophy of the muscle fibers in heart 10, particularly those surrounding left ventricle 14.

Figure 1B:
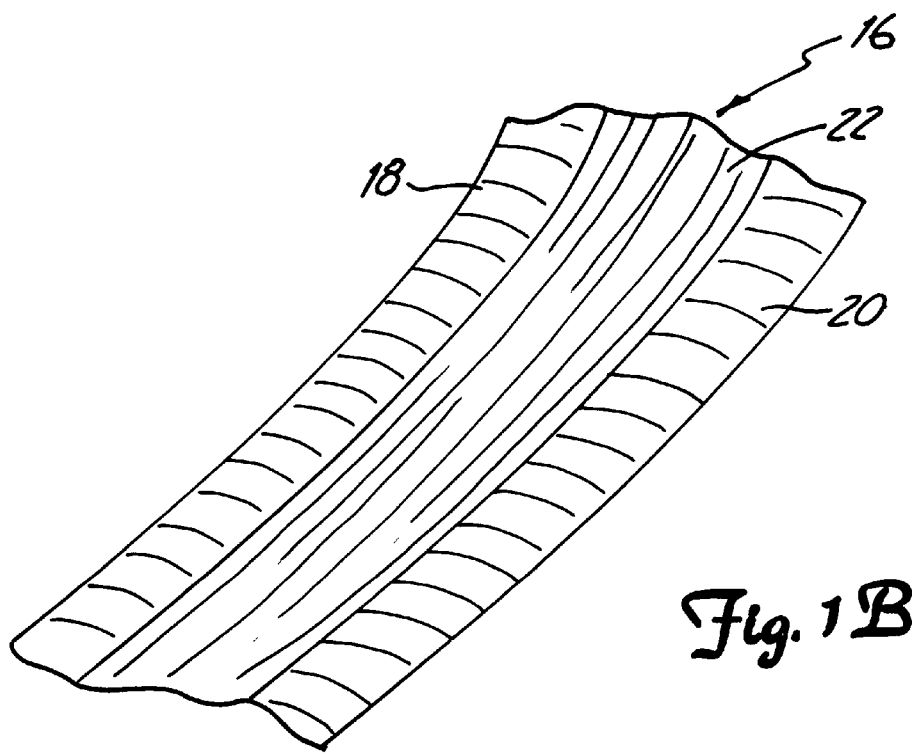
FIG. 1B is a greatly enlarged sectional view of a portion of the heart shown in FIG. 1A.

FIG. 1B illustrates a greatly enlarged sectional view of a portion of wall 16 of heart 10 shown in FIG. 1A. FIG. 1B is taken from the portion labeled 1B in FIG. 1A. FIG. 1B illustrates that wall 16 is formed of an endocardium layer 18 which comprises the inner tissue of heart wall 16. Heart wall 16 also includes an epicardium layer 20 which comprises the outer tissue in heart wall 16. Mid-wall portion 22 comprises a portion of wall 16 between the endocardium 18 and epicardium 20. The pericardium is a double-walled sac which encloses the heart. The inner layer of the pericardial sac comprises the epicardium 20.

Photomicrographs available from the American Heart Association libraries show that the alignment of cardiac muscle fibers are generally perpendicular to the ventricular cavity wall in the endocardium 18 and epicardium 20. Also, the muscle fibers are typically nearly parallel to the ventricular cavity wall in the mid-wall portion 22. During hypertrophy of the muscular wall 16 around the left ventricle 14, the muscle fibers stretch and elongate in a direction generally parallel to their longitudinal orientation. Thus, the muscle fibers in the endocardium 18 and epicardium 20 elongate in a direction generally perpendicular to the ventricular cavity wall. Also, the muscle fibers in the mid-wall region 22 elongate in a direction generally parallel to the ventricular cavity wall. Additional muscle fibers also develop. All of these effects contribute to an increase in muscle mass and stretching of the heart muscle fibers.

Figure 2:
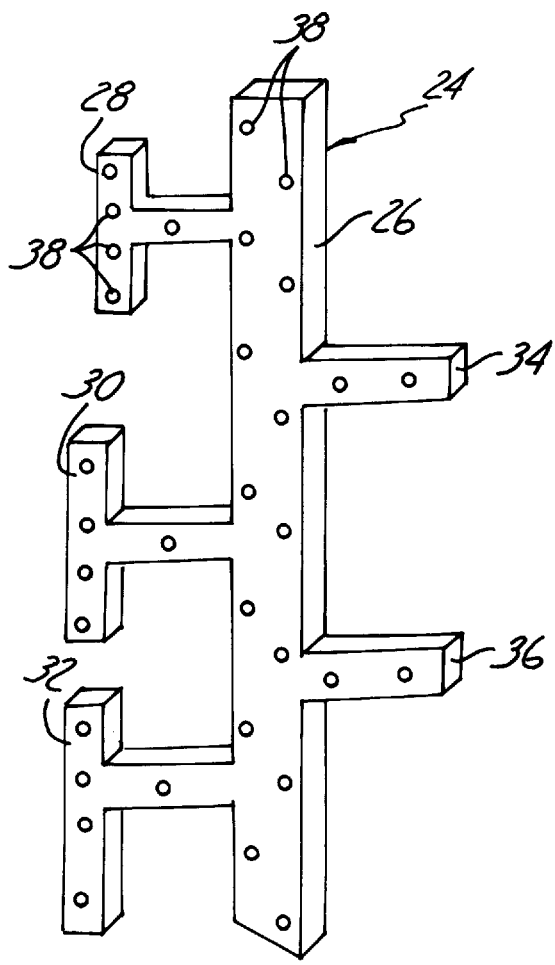
FIG. 2 illustrates a retention strip in accordance with one aspect of the present invention.

FIG. 2 illustrates a retention strip 24 in accordance with one aspect of the present invention. Retention strip 24, in one preferred embodiment, includes a generally longitudinal strut 26 with a first set of protrusions 28, 30 and 32 extending from strut 26 in a first direction and a second plurality of protrusions 34 and 36 extending from longitudinal strut 26 in a second direction, generally opposite the first direction. While protrusions 28, 30 and 32 are shown to have a generally T-shaped conformation, and while protrusions 34 and 36 have a generally linear conformation, it should be noted that all of struts 28–36 could either have a T conformation or a linear conformation.

Retention strip 24 is also shown having a plurality of apertures 38 which are used for suturing retention strip 24 in place. Of course, the number and placement of the suture apertures 38 shown in FIG. 2 is illustrative only. More or less apertures 38, and apertures having different placement on retention strip 24 are contemplated as well.

Also, while only three protrusions 28, 30, and 32 are shown and two protrusions 34 and 36 are shown, any suitable number of protrusions can be used on either side of retention strip 24. Strut 26 and protrusions 28, 30, 32, 34, and 36 are preferably formed of a material which allows repeated bending cycles, without permanent deformation or breakage. However, strut 26 and protrusions 28, 30, 32, 34, and 36 are also preferably formed of a material which exhibits high resistance to elongation in the longitudinal direction. Suitable materials include collagen, or biocompatible and implantable polymer strips, as well as biocompatible and implantable metals, cartilage, or composite materials, Nitinol and bovine and porcine byproducts, as examples.

Figure 3:
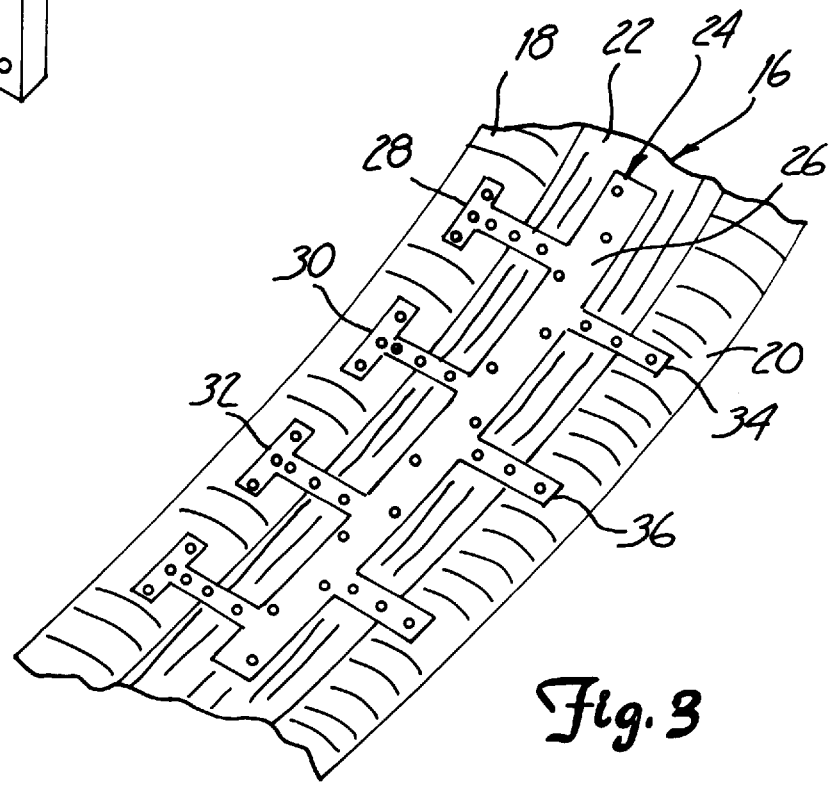
FIG. 3 illustrates the retention strip shown in FIG. 2 embedded in the heart wall.

FIG. 3 illustrates a portion of wall 16 with retention strip 24 implanted therein. In a preferred embodiment, longitudinal strut 26 is implanted in the mid-wall region 22 of wall 16. Protrusions 28, 30 and 32 (and any other number of protrusions) extend into the endocardium layer 18, while protrusions 34 and 36 (and any other suitable number of protrusions) extend into the epicardium layer 20. Retention strip 24 is then sutured in place by an appropriate suturing technique using apertures 38 in retention strip 24. Retention strip 24 preferably extends throughout substantially the entire longitudinal length of the ventricular cavity wall, such as from the base to the apex of the ventricular cavity wall.

Figure 4:
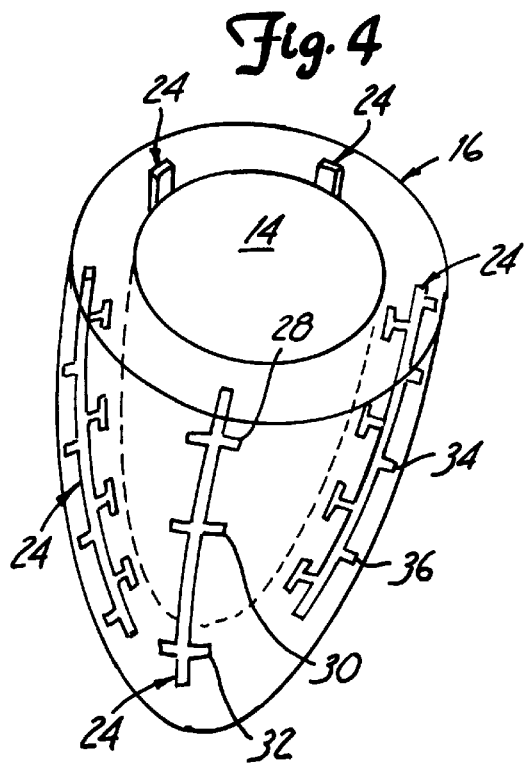
FIG. 4 illustrates a plurality of the strips as shown in FIG. 2 embedded in the wall of the left ventricle.

FIG. 4 illustrates a plurality of retention strips 24 embedded in wall 16 about left ventricle 14. Retention strips 24 are preferably arranged at regular intervals about left ventricle 14 to encircle left ventricle 14 in wall 16. Such placement forms a restrictive cage around left ventricle 14 of heart 10. Strips 24 thus provide very little, or no impedance to the natural contractile motion of the heart. However, fixturing of retention strips 24 to the tissue of the heart with sutures prevents enlargement or substantially eliminates enlargement and extensive stretch of the muscle fibers.

Since longitudinal strut 26 is substantially resistant to elongation in its longitudinal direction, it helps to prevent elongation of the muscle fibers in mid-wall region 22. Also, since protrusions 28, 30 and 32 are highly resistant to elongation in their longitudinal directions, they greatly inhibit elongation or stretch of the muscle fibers in endocardium layer 18. Similarly, since protrusions 34 and 36 are highly resistant to elongation in their longitudinal direction, they greatly inhibit elongation or stretch of the muscle fibers in epicardium layer 20.

Placement of retention strips 24 in the positions illustrated in FIG. 4 thus restrict the progression of congestive heart failure of the muscle due to the pressure overload on left ventricle 14. The muscle is supported in such a way that it is not allowed to progressively increase its mass, and also such that uncontrolled stretching is limited by physically restricting its growth and stretch. Thus, heart failure can be controlled. Further, since the recruitable muscle mass can still perform a satisfactory job due to the limited constraint on its contraction, no additional or compensatory muscle mass is generated, which also restricts growth of new muscle tissue in wall 16. This aspect of the present invention thus reduces fatigue of the heart muscle and allows for natural regeneration of healthy cardiac tissue. Also, it is believed that supporting the cardiac muscle tissue relives tension on the chordae tendinae which, in turn, helps prevent mitral valve regurgitation which prevents higher mean atrial pressures and thus pulmonary edema.

Figure 5:
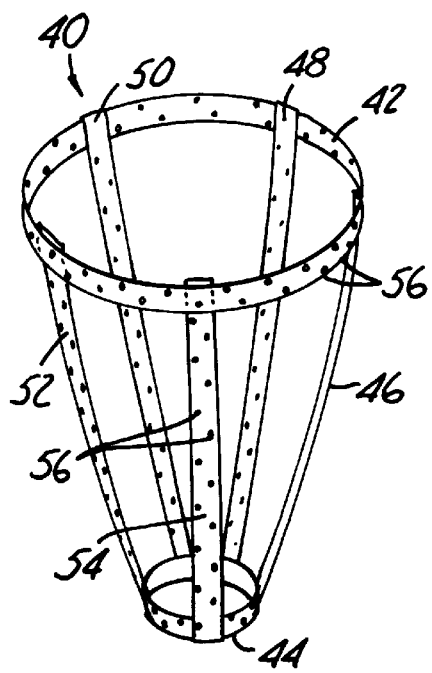
FIG. 5 illustrates a second embodiment of a retention mechanism in accordance with one aspect of the present invention.

FIG. 5 illustrates another embodiment of a retention device 40 in accordance with another aspect of the present invention. With progressive congestive heart failure, heart 10 may already have started to hypertrophy and thus may be vulnerable to trauma. Thus, extensive incision in heart 10 may be undesirable. In that case, retention device 40 can be used by attaching it to the epicardial surface of heart 10 with only minimal intrusion into the heart muscle (such as with sutures, adhesives, staples, or other connection techniques).

Retention device 40 includes a first generally circular strap 42 and a second generally circular strap 44. Straps 42 and 44 are connected to one another by a plurality of generally longitudinal straps 46, 48, 50, 52 and 54. Straps 46, 48, 50, 52, and 54 are preferably attached to circular strips 42 and 44 by a suitable adhesive, by welding, or by another suitable mechanism, or are formed integrally with circular straps 42. Straps 42, 44, 46, 48, 50, 52, and 54 are preferably formed of collagen, polymer or metal fibers which exhibit the capability of undergoing many bending cycles, without permanent deformation of damage. Straps 42, 44, 46, 48, 50, 52, and 54 are also formed to exhibit high resistance to elongation in the generally longitudinal directions. In addition, straps 42, 44, 46, 48, 50, 52, and 54 have a plurality of apertures 56 therein which are used to attach retention device 40 to the heart wall 16 with an appropriate suturing technique. Of course, as with the embodiment illustrated in FIGS. 2–4, any suitable number of straps 42, 44, 46, 48, 50, 52, and 54 can be used. The arrangement of straps 42, 44, 46, 48, 50, 52, and 54 can also be changed as desired. Further, the number and placement of suture apertures 56 can be changed to any suitable number and location on straps 42, 44, 46, 48, 50, 52, and 54.

Figure 6B:
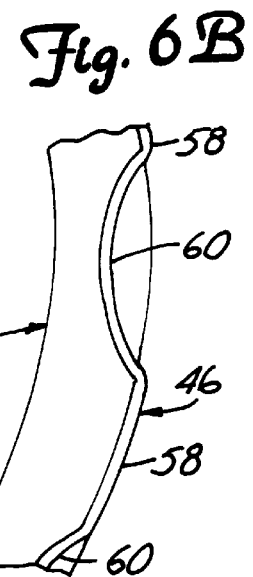
FIG. 6B is a sectional view of a portion of the heart wall shown in FIG. 6A.
Figure 6A:
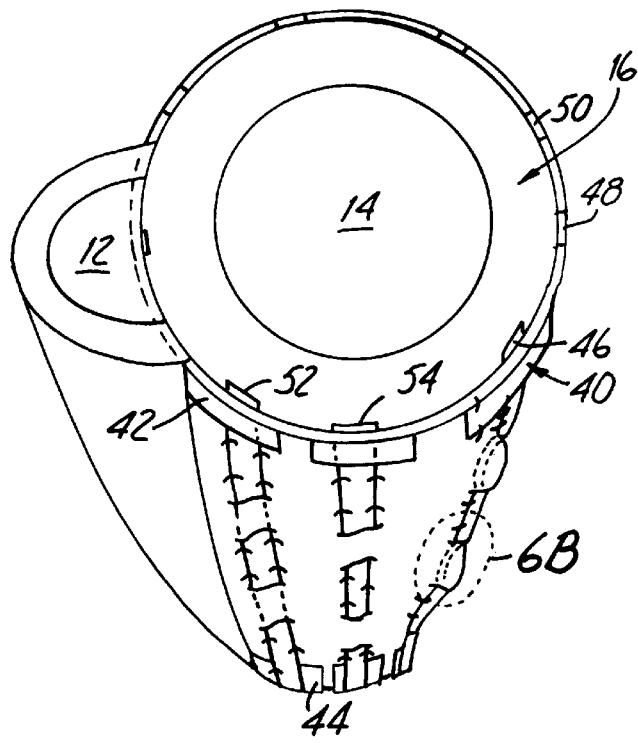
FIG. 6A shows the retention mechanism illustrated in FIG. 5 deployed on the outer surface of the left ventricle.

FIG. 6A illustrates retention device 40 deployed on wall 16 of left ventricle 14. FIG. 6A illustrates that, in one preferred embodiment, straps 42, 44, 46, 48, 50, 52, and 54 are periodically, and alternately, sutured to the outer surface of epicardium 20, and embedded within wall 16. FIG. 6A also illustrates that more longitudinal straps can be used than are illustrated in FIG. 5. This simply illustrates that any desired number of longitudinal straps can be used. In the preferred embodiment, in the areas where straps 42, 44, 46, 48, 50, 52, and 54 are embedded in wall 16, they are embedded only in the epicardium layer 20 such that extensive incisions into wall 16 need not be made.

FIG. 6B better illustrates embedding of straps 42, 44, 46, 48, 50, 52, and 54 in the wall 16 of heart 10. FIG. 6B is a greatly enlarged cross-section of wall 16 taken in the region labeled 6B in FIG. 6A. FIG. 6B illustrates that strap 46, at alternate portions 58 is simply sutured to the exterior of epicardium layer 20, while at other portions 60 is embedded within the epicardium layer 20. Of course, straps 42, 44, 46, 48, 50, 52, and 54 could be embedded more deeply in the wall 16. However, embedding in epicardial layer 20 is preferred.

As with the embodiment illustrated in FIGS. 2–4, retention device 40 restricts the progression of failure of heart muscle 16 due to pressure overload on the left ventricle 14 of heart 10. Heart 10 is not allowed to progressively increase its mass and since the uncontrolled stretching of the heart muscle is physically restricted, heart failure can be controlled. Further, since the recruitable muscle mass is still capable of operating satisfactorily, no additional, compensatory muscle mass needs to be generated. Retention device 40 thus restricts growth of new muscle. Further, retention device 40 allows for minimal internal damage to heart 10.

Figure 7:
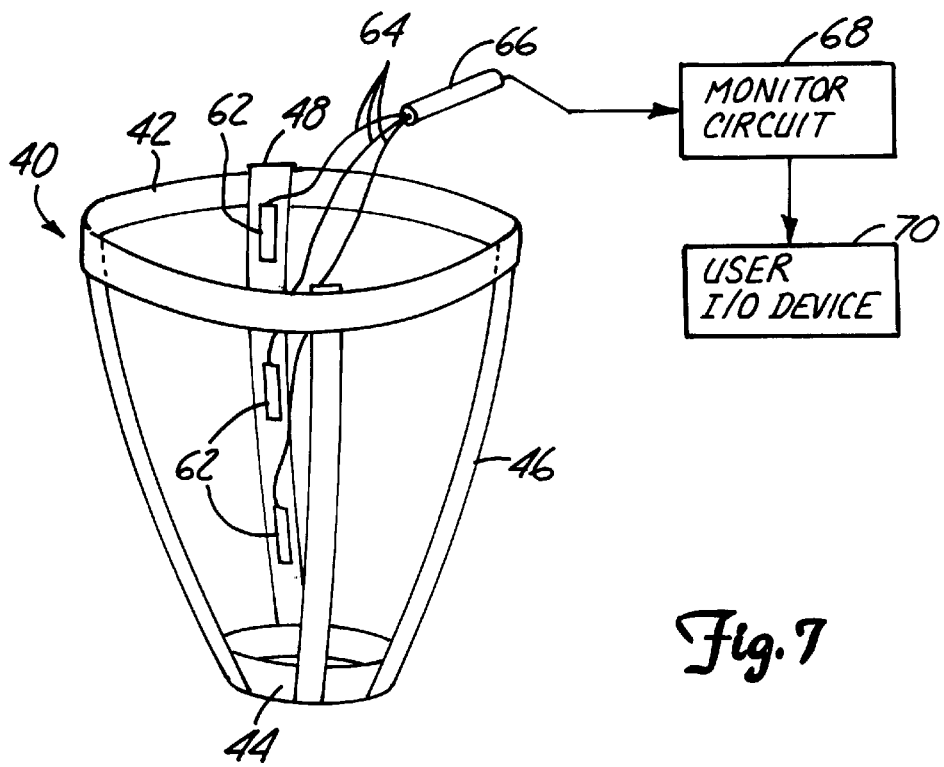
FIG. 7 illustrates another embodiment of a monitoring system in accordance with one aspect of the present invention.

FIG. 7 illustrates another embodiment of retention device 40 in accordance with one aspect of the present invention. Retention device 40, shown in FIG. 7, is similar to that shown in FIG. 5, and similar items are similarly numbered. However, the longitudinal straps 42, 44, 46, 48, 50, 52, and 54 (only four of which are shown in FIG. 7) are each provided with a plurality of sensors 62 which are configured to sense stretching, and/or other physiologic parameters, such as electrical activity, acceleration or physicochemical activity, of the cardiac muscle wall 16. In the illustration of FIG. 7, sensors 62 are only provided on longitudinal strap 48, it will be appreciated that, in a preferred embodiment, sensors 62 are similarly disposed on each of the straps 42, 44, 46, 48, 50, 52, and 54.

Sensors 62 are preferably wire bond strain gauges, piezopolymer strips, or other strain measuring sensors. As is generally known, some such strain gauges are provided with a resistive bridge having a signal, such as a voltage, applied thereacross. As strain on the bridge changes, the values of signals received from the bridge change in a differential manner. In piezopolymer elements, application of a mechanical stress to the device generates electric polarization which can also be sensed. Thus, each sensor 62 provides one or more conductors 64 which carry signals indicative of the stretching of muscle wall 16. Such conductors are preferably provided through a suitable cable 66 to monitor circuit 68 which, in turn, is coupled to a user input/output (I/O) device 70.

In one preferred embodiment, the strain information captured by the signals conducted by conductors 64 to monitor circuit 68 is processed to obtain a total stretch response in the myocardium of heart 10. Such processing preferably occurs in monitor circuit 68 and is described below. The total stretch response is preferably monitored for variations and thus provides information about the stretching and condition of heart 10. This information is preferably used for the treatment and management of the heart failure condition, either by itself through observation, or used to generate a feedback signal which can be used to pace heart 10 for maximal contraction (which is described in greater detail with respect to FIG. 9).

User I/O device 70 is preferably any suitable I/O device, such as a cathode ray tube, an LCD display, a strip or other printer, or any other suitable I/O device. I/O device 70 may also allow user input functions by including a keypad, a keyboard, or other user actuable elements.

Figure 8:
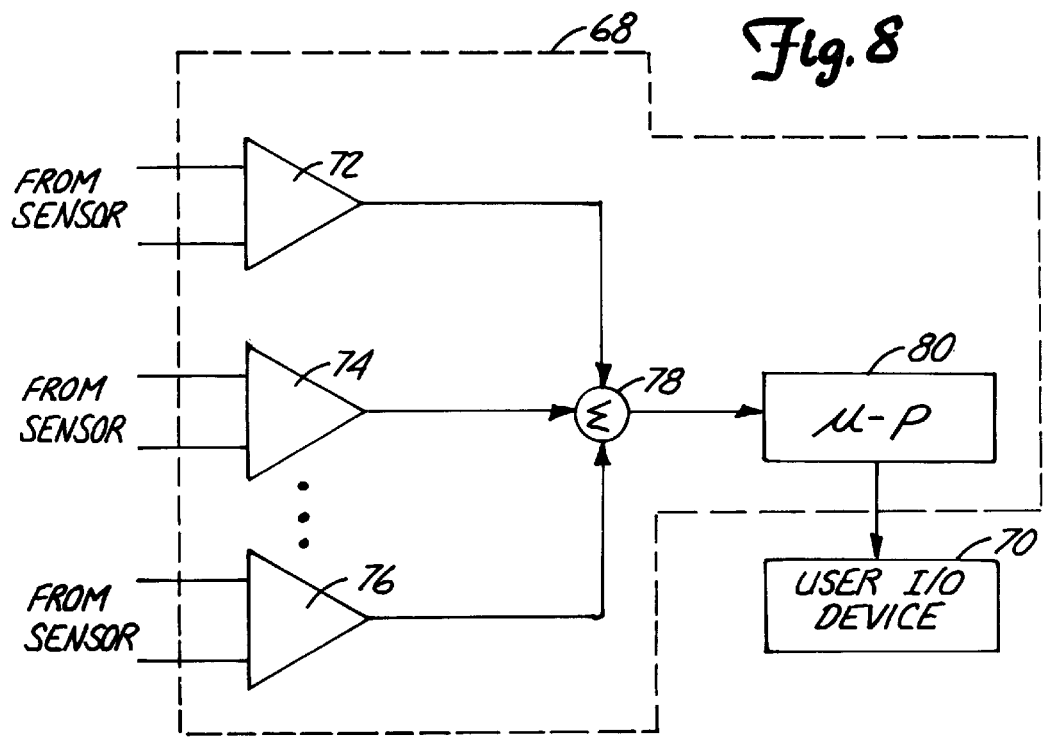
FIG. 8 illustrates a portion of the monitoring system shown in FIG. 7 in schematic and partial block diagram form.

FIG. 8 illustrates a more detailed block diagram of one embodiment of monitor circuit 68. Monitor circuit 68 preferably includes a plurality of differential amplifiers 72, 74 and 76, a circuit (such as a summing amplifier, multiplexer, etc.) 78 and a microprocessor or microcontroller based circuit 80. Of course, monitor circuit 68 may also include other signal filtering and amplification, and other general signal conditioning circuitry, which is generally known for conditioning signals from strain sensors and is not described here in detail.

In the embodiment illustrated in FIG. 8, differential amplifiers 72, 74, and 76 are provided for amplifying the signals received from strain sensors 62. In one preferred embodiment, each strain sensor 62 has a corresponding differential amplifier. Alternatively, of course, multiplexing circuitry can be used to switch the signals from sensors 62 into a single, or into one or more of the differential amplifiers. In any case, the output signals from differential amplifiers 72, 74, and 76 are provided to circuit 78. In the embodiment in which circuit 78 is a summing amplifier, the signals are summed in a desired manner to obtain the total stretch response of the myocardium of heart 10. The signal from amplifier 78 is provided to microprocessor 80 where it is preferably corrected for any non-linearities and temperature affects, in a known manner. Microprocessor 80 then generates a suitable output signal to user I/O device 70.

In another embodiment in which circuit 78 is a multiplexer, each of the signals from amplifiers 72, 74, and 76 are switched into microprocessor 80 under the control of microprocessor 80. Alternatively, circuit 78 can also be eliminated. In that embodiment, the outputs from amplifiers 72, 74, and 76 are provided as discrete inputs to microprocessor 80. It should also be noted that other inputs can be provided to microprocessor 80 as well, such as EKG information, blood pressure information, or other sources of information. In any case, microprocessor 80 generates a signal to user I/O device 70 based on the signals from amplifiers 72, 74, and 76.

Figure 9:
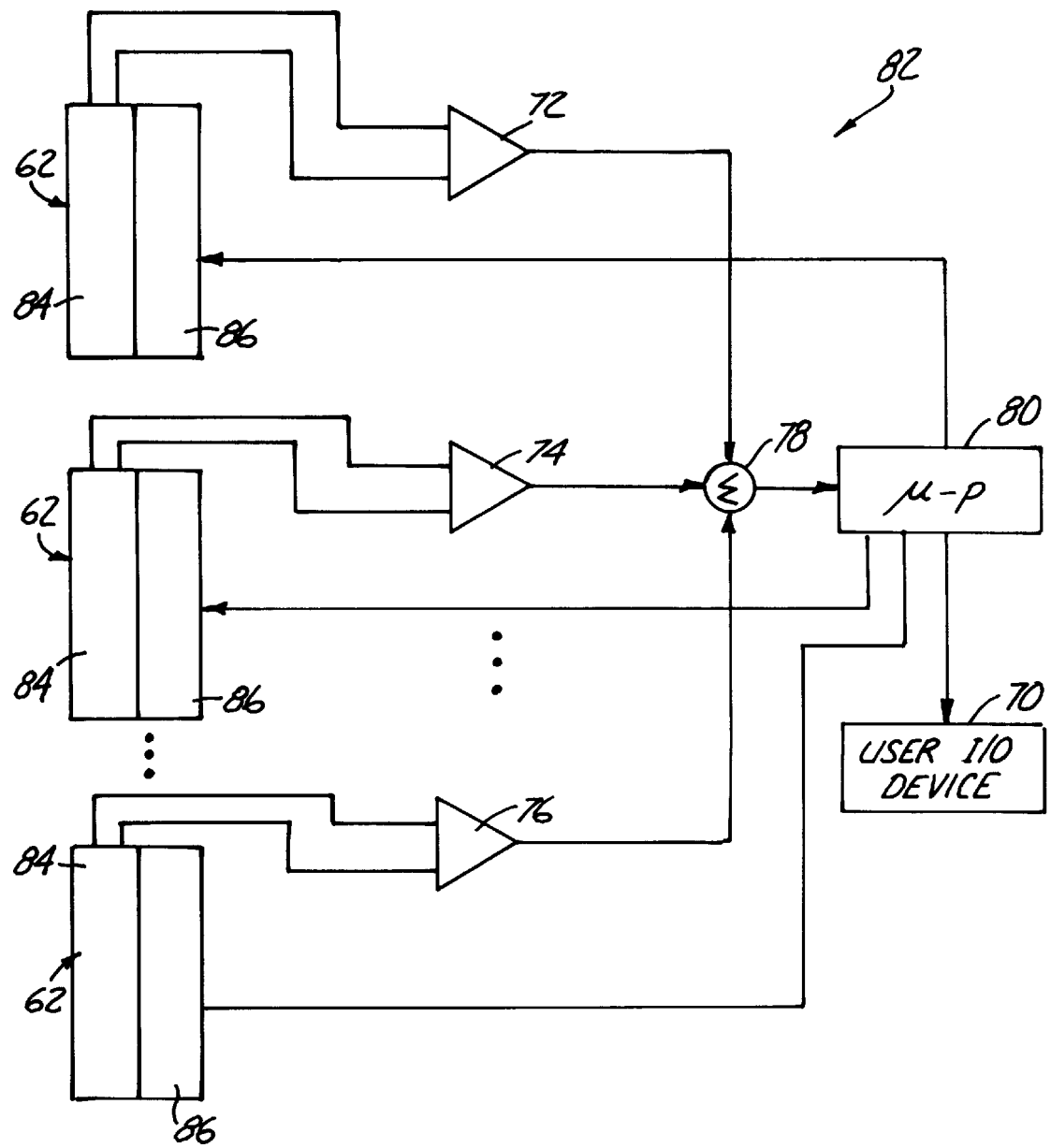
FIG. 9 illustrates another embodiment of a monitoring and control system in schematic and partial block diagram form.

FIG. 9 illustrates another embodiment of a monitoring and control system 82 in accordance with one aspect of the present invention. Some items in system 82 are similar to those shown in FIGS. 7 and 8 and are similarly numbered. In system 82, each sensor 62 is provided with a strain sensing element 84, as discussed above, and an excitation electrode 86. Excitation electrodes 86 are preferably conventional pacing electrodes capable of delivering pacing voltages to the myocardium of heart 10. While the sensing elements 84 and pacing electrodes 86 are shown attached to one another in FIG. 9, it should be noted that they can be separated from one another, but are preferably closely proximate one another when deployed on one of straps 42, 44, 46, 48, 50, 52, and 54.

In one preferred embodiment, microprocessor 80 receives the stretch response information from sensor elements 84 which indicates not only long term stretching of the heart muscle fibers, but which also indicates contractile motion of the heart 10 in a pulsatile fashion. Based upon this information, microprocessor 80 generates a plurality of feedback signals which are provided to each of pacing electrodes 86. The feedback signals are used to energize pacing electrodes 86 to deliver the necessary pacing voltages to the myocardium of heart 10 in order to pace heart 10.

In one preferred embodiment, microprocessor 80 simply energizes all of electrodes 86 at one time to cause contraction of the heart muscle. In another preferred embodiment, however, the microprocessor 80 selectively and sequentially energizes each of the excitation electrodes 86 in order to sequentially pace different sets of electrodes 86 to achieve optimal contraction of the ventricles. In that embodiment, the output of each of differential amplifiers 72, 74 and 76 can be individually provided to microprocessor 80, as well as through, for example, a summing amplifier 78. Microprocessor 80, in a preferred embodiment, also calculates and delivers appropriate pacing voltages to the various sets of excitation electrodes 86 being controlled.

As with the other embodiments discussed herein, system 82, when used in conjunction with retention device 40 restricts the progression of failure of the muscle of heart 10 due to the pressure overload in the left ventricle 14. The muscle in heart 10 is preferably supported such that it is not allowed to progressively increase its mass, and so as to restrict uncontrolled stretch of the heart muscle in order to control heart failure. Since the muscle is not allowed to reach a point of destructive stretching, the muscle fibers maintain their inherent contractile properties (actin-myosin overlap) and the progression to failure (or cascade) can be stopped. Also, since the recruitable muscle mass is still performing satisfactorily, no additional or compensatory muscle mass needs to be generated, thus further restricting growth of new muscle.

In another preferred embodiment, the present invention is used to deliver a drug or other therapeutic agent to the tissue with which it is used. For example, in one embodiment, the struts, protrusions, retention strips, etc. are coated or impregnated with or otherwise provided with the therapeutic agent which is preferably engineered to be released into the adjacent tissue over time. Such drugs or therapeutic agents illustratively include genetic therapeutic agents like growth factors, angiogenics, angiotensin converting enzymes, or contractibility promoters (such as that sold under the name Digitalis) or other suitable drugs.

In addition, it is believed that the heart muscle can benefit from suturing or other manipulations of the heart muscle in accordance with the present invention. This benefit results from myocardial revascularization which is a known angiogenic effect which regenerates cardiac tissue.

The present invention reduces fatigue of the heart and allows for natural regeneration of healthy cardiac tissue, or increases the efficiency of pharmacologically administered treatments. It is also believed that supporting the cardiac muscle in this way relieves tension on the chordae tendinae which in turn prevents mitral valve regurgitation thus preventing higher mean atrial pressures and pulmonary edema. All of these factors contribute to the cascade of failures in organs and systems associated with congestive heart failure. Once the relaxed heart muscle has regained many of its own contractile properties, it can be weaned from the pacing routine.

It should also be noted that the present invention contemplates implementing the techniques and devices described herein not only on the left ventricle, but also on the right ventricle or the other chambers of the heart. Further, the present invention can be implemented on any desired combination of chambers.

Although the present invention has been described with reference to preferred embodiments, workers skilled in the art will recognize that changes may be made in form and detail without departing from the spirit and scope of the invention.

What is claimed is:

1. An apparatus for relieving stress of heart muscle tissue in a wall of a heart having a chamber, the muscle tissue having an epicardium layer, an endocardium layer and a midwall portion between the epicardium and endocardium layers, the epicardium layer, the endocardium layer and the midwall portion extending generally longitudinally to form the wall of the heart, the apparatus comprising:

a plurality of biocompatible and implantable elongate strips, elongate in a longitudinal direction, configured to be connected to the heart wall and disposed about the chamber such that the elongate strips are arranged in spaced relation to one another, the elongate strips being bendable and being sufficiently resistant to elongation that natural stretching of the heart wall does not cause elongation of the plurality of strips.

2. The apparatus of claim 1 wherein the elongate strips are resistant to elongation in the longitudinal direction.

3. The apparatus of claim 1 wherein each of the elongate strips comprises:
   a longitudinal strut; and
   a first plurality of protrusions extending from the longitudinal strut in a first direction, the first protrusions being sufficiently resistant to elongation in the first direction such that natural stretching of the heart wall does not cause elongation of the first protrusions in the first direction.

4. The apparatus of claim 3 wherein each of the elongate strips comprises:
   a second plurality of protrusions extending from the longitudinal strut in a second direction, generally opposite the first direction, the second protrusions being sufficiently resistant to elongation in the second direction such that natural stretching of the heart wall does not cause elongation of the second protrusions in the second direction.

5. The apparatus of claim 4 wherein the longitudinal strut and the first and second protrusions are arranged such that when the longitudinal strut is positioned longitudinally in the midwall portion, the first protrusions extend into the epicardium layer and the second protrusions extend into the endocardium layer.

6. The apparatus of claim 5 wherein the first protrusions have a generally linear conformation.

7. The apparatus of claim 5 wherein the second protrusions have a generally T-shaped conformation.

8. The apparatus of claim 5 wherein the longitudinal strut and the first and second protrusions define a plurality of apertures suitable for receiving sutures.

9. The apparatus of claim 1 wherein the plurality of elongate strips are connected to the epicardium layer.

10. The apparatus of claim 9 wherein the plurality of strips are connected to one another, in spaced relation to one another to from a cage structure sized to be disposed about the chamber.

11. The apparatus of claim 10 wherein the plurality of strips carry a plurality of sensors configured to sense physiological parameters in the wall of the heart and provide sensor signals indicative of the sensed parameters.

12. The apparatus of claim 11 wherein the plurality of sensors are configured to sense stretching of the wall of the heart and provide the sensor signals indicative of the sensed stretching.

13. The apparatus of claim 12 and further comprising:
   a monitor coupled to the plurality of sensors to receive the sensor signals and provide a monitor signal based on the sensor signals; and
   an input/output device, coupled to the monitor, to receive the monitor signal and provide user observable indicia, indicative of the sensed stretching based on the monitor signal.

14. The apparatus of claim 13 and further comprising:
   a plurality of electrodes carried by the plurality of strips; and
   wherein the monitor includes a controller coupled to the electrodes to control application of excitation signals to the electrodes, the electrodes stimulating the heart muscle in response to the excitation signals.

15. The apparatus of claim 14 wherein the controller is coupled to the sensors and is configured to apply the excitation signals based on the sensor signals.

16. The apparatus of claim 15 wherein the controller is configured to apply the excitation signals to all electrodes substantially simultaneously.

17. The apparatus of claim 15 wherein the controller is configured to apply the excitation signals to the electrodes sequentially.

18. The apparatus of claim 17 wherein the controller is configured to apply the excitation signals to sets of the electrodes sequentially.

19. The apparatus of claim 11 wherein the strips define a plurality of apertures therein sized to receive sutures.

20. The apparatus of claim 1 wherein the elongate strips include a drug releasably coupled thereto.

21. A method of restricting elongation of heart muscle tissue in a wall of a heart having a chamber, the muscle tissue having an epicardium layer, an endocardium layer and a midwall portion between the epicardium and endocardium layers, the epicardium layer, the endocardium layer and the midwall portion extending generally longitudinally to form the wall of the heart, the method comprising:
   providing a plurality of biocompatible and implantable elongate strips, elongate in a longitudinal direction, the elongate strips being bendable and being sufficiently resistant to elongation in the longitudinal direction such that natural stretching of the heart wall does not cause elongation of the plurality of strips; and
   connecting the elongate strips to the heart wall and about the chamber such that the elongate strips are arranged in spaced relation to one another.

22. The method of claim 21 wherein providing a plurality of elongate strips comprises providing the elongate strips such that each of the elongate strips comprises:
   a longitudinal strut;
   a first plurality of protrusions extending from the longitudinal strut in a first direction, the first protrusions being sufficiently resistant to elongation in the first direction such that natural stretching of the heart wall does not cause elongation of the first protrusions in the first direction; and
   a second plurality of protrusions extending from the longitudinal strut in a second direction, generally opposite the first direction, the second protrusions being sufficiently resistant to elongation in the second direction such that natural stretching of the heart wall does not cause elongation of the second protrusions in the second direction.

23. The method of claim 22 wherein connecting the elongate strips to the heart comprises:
   implanting the longitudinal strut longitudinally in the midwall portion;
   arranging the strip such that the first protrusions extend into the epicardium layer and the second protrusions extend into the endocardium layer; and
   attaching the longitudinal strut and the first and second protrusions to surrounding tissue in the heart wall.

24. The method of claim 23 wherein attaching comprises:
   attaching utilizing a method which promotes revascularization of the tissue in the heart wall.

25. The method of claim 23 wherein the longitudinal strut and the first and second protrusions define a plurality of apertures, and wherein attaching comprises:
   suturing the longitudinal strut and the first and second protrusions to the surrounding tissue through the apertures.

26. The method of claim 21 wherein the plurality of strips are connected to one another, in spaced relation to one another to from a cage structure, and wherein connecting comprises:

attaching the cage structure to the heart wall around the chamber.

27. The method of claim 26 wherein attaching comprises:

implanting first portions of the strips in the heart wall; and connecting second portions of the strips between the between the first portions, to an exterior surface of the epicardium layer.

28. The method of claim 27 wherein implanting comprises:

implanting the first portions in the epicardium layer.

29. The method of claim 26 wherein providing a plurality of strips comprises:

providing a plurality of sensors carried by the elongate strips;

sensing, with the sensors, stretching of the wall of the heart; and providing sensor signals indicative of the sensed stretching.

30. The method of claim 29 and further comprising:

providing user observable indicia, indicative of the sensed stretching, based on the sensor signals.

31. The method of claim 30 wherein providing a plurality of elongate strips further comprises:

providing a plurality of electrodes carried by the plurality of strips; and controlling application of excitation signals to the electrodes, the electrodes stimulating the heart muscle in response to the excitation signals.

32. The method of claim 31 wherein controlling application of excitation signals comprises:

applying the excitation signals based on the sensor signals.

33. The method of claim 32 wherein applying the excitation signals comprises:

applying the excitation signals to all electrodes substantially simultaneously.

34. The method of claim 32 wherein applying the excitation signals comprises:

applying the excitation signals to the electrodes sequentially.

35. The method of claim 34 wherein applying the excitation signals sequentially comprises:

applying the excitation signals to sets of the electrodes sequentially.

36. The method of claim 26 wherein the strips define a plurality of apertures, and wherein attaching the cage structure comprises:

suturing the strips to the heart wall through the apertures.

* * * * *

UNITED STATES PATENT AND TRADEMARK OFFICE
CERTIFICATE OF CORRECTION

PATENT NO. : 6,110,100
DATED : August 29, 2000
INVENTOR(S) : Dnyanesh Talpade

It is certified that error appears in the above-identified patent and that said Letters Patent is hereby corrected as shown below:

<u>Title page,</u>
Item [56], References Cited, U.S. PATENT DOCUMENTS, insert:
-- 3,983,863     10/1976          JANKE, et al.    128/1R
   3,827,426     8/1974           PAGE, et al.     128/1D --

FOREIGN PATENT DOCUMENTS, insert:
-- O 303 719        2/1989         EPO
   WO 98/29041      7/1998         PCT Publication
   WO 97/24101      7/1997         PCT Publication
   WO 98/58598      12/1998        PCT Publication
   WO 98/55165      12/1998        PCT Publication
   WO 98/03213      1/1998         PCT Publication --

Signed and Sealed this

Sixth Day of May, 2003

JAMES E. ROGAN
*Director of the United States Patent and Trademark Office*